United States Patent [19]
Reynolds

[11] Patent Number: 5,985,081
[45] Date of Patent: Nov. 16, 1999

[54] PROCESS FOR MAKING A SHAPED PRODUCT WITH NO MATERIAL WASTE

[75] Inventor: Gary Mack Reynolds, Woodstock, Ga.

[73] Assignee: Kimberly-Clark Worldwide, Inc., Neenah, Wis.

[21] Appl. No.: 09/105,629

[22] Filed: Jun. 26, 1998

[51] Int. Cl.$^6$ .................................................. B32B 31/18
[52] U.S. Cl. ...................... 156/271; 156/324; 156/516; 264/146
[58] Field of Search ................................ 156/269, 271, 156/324, 516, 510; 264/146, 160

[56] References Cited

U.S. PATENT DOCUMENTS

| | | |
|---|---|---|
| 4,081,301 | 3/1978 | Buell . |
| 4,249,532 | 2/1981 | Polansky et al. . |
| 4,341,216 | 7/1982 | Obenour . |
| 4,534,769 | 8/1985 | De Jonckheere et al. . |
| 4,595,441 | 6/1986 | Holvoet et al. . |
| 4,666,542 | 5/1987 | De Jonckheere . |
| 4,687,477 | 8/1987 | Suzuki et al. . |
| 4,699,620 | 10/1987 | Bernardin . |

(List continued on next page.)

FOREIGN PATENT DOCUMENTS

| | | |
|---|---|---|
| 2186664 A1 | 3/1997 | Canada . |
| 0 768 073 A1 | 4/1997 | European Pat. Off. . |
| 92/6027 | 8/1992 | South Africa . |
| WO 88/06008 A1 | 8/1988 | WIPO . |
| WO 93/03698 A1 | 3/1993 | WIPO . |
| WO 94/28844 A2 | 12/1994 | WIPO . |
| WO 95/02384 A1 | 1/1995 | WIPO . |
| WO 96/19166 A1 | 6/1996 | WIPO . |
| WO 96/22064 A1 | 7/1996 | WIPO . |
| WO 96/31179 A3 | 10/1996 | WIPO . |
| WO 96/32083 A1 | 10/1996 | WIPO . |
| WO 97/00056 A1 | 1/1997 | WIPO . |
| WO 97/14385 A1 | 4/1997 | WIPO . |
| WO 97/24094 A1 | 7/1997 | WIPO . |
| WO 97/24283 A1 | 7/1997 | WIPO . |

*Primary Examiner*—Daniel Stemmer
*Attorney, Agent, or Firm*—Paul Yee

[57] ABSTRACT

A distinctive technique for creating a shaped article (90, 100) includes a pivoting of a first portion (56) of a cooperating web layer (26) substantially about a first joining region (40) to lie laterally adjacent to a first portion (52) of a primary web layer (24). The cooperating web layer (26) has been positioned in a superposed facing relation with the primary web layer (24) with the primary web layer having a first and second, lateral side edge regions (32, 34), and the cooperating web layer having third and fourth, lateral side edge regions (36, 38). The first side edge region (32) of the primary web layer (24) has been synchronized to the third side edge region (36) of the cooperating web layer (26) along the first joining region (40), and the second side edge region (34) of the primary web layer (24) has been synchronized to the fourth side edge region (38) of the cooperating web layer (26) along a second joining region (42) to provide a synchronized laminated web (44). The laminated web has been separated along a serpentine division line (46) to provide a first composite web (48) and at least a second composite web (50). The first composite web (48) has the first portion (52) of the primary web layer (24) combined with the first portion (56) of the cooperating web layer (26), and the second composite web (50) has a second portion (54) of the primary web layer (24) combined with a second portion (58) of the cooperating web layer (26).

20 Claims, 13 Drawing Sheets

U.S. PATENT DOCUMENTS

| | | |
|---|---|---|
| 4,701,172 | 10/1987 | Stevens . |
| 4,701,173 | 10/1987 | Zehner et al. . |
| 4,701,175 | 10/1987 | Boland et al. . |
| 4,710,187 | 12/1987 | Boland et al. . |
| 4,731,066 | 3/1988 | Korpman . |
| 4,753,646 | 6/1988 | Enloe . |
| 4,762,582 | 8/1988 | De Jonckheere . |
| 4,883,480 | 11/1989 | Huffman et al. . |
| 4,938,754 | 7/1990 | Mesek . |
| 4,950,262 | 8/1990 | Takagi . |
| 5,019,066 | 5/1991 | Freeland et al. . |
| 5,026,364 | 6/1991 | Robertson . |
| 5,034,007 | 7/1991 | Igaue et al. ............................ 604/365 |
| 5,037,416 | 8/1991 | Allen et al. . |
| 5,061,261 | 10/1991 | Suzuki et al. ........................ 604/385.2 |
| 5,098,423 | 3/1992 | Pieniak et al. . |
| 5,110,386 | 5/1992 | Ochi et al. ............................... 156/204 |
| 5,133,707 | 7/1992 | Rogers et al. . |
| 5,263,948 | 11/1993 | Karami et al. . |
| 5,263,949 | 11/1993 | Karami et al. . |
| 5,269,775 | 12/1993 | Freeland et al. . |
| 5,399,219 | 3/1995 | Roessler et al. ........................ 156/259 |
| 5,527,303 | 6/1996 | Milby, Jr. et al. . |
| 5,531,730 | 7/1996 | Dreier . |
| 5,542,942 | 8/1996 | Kline et al. . |
| 5,558,660 | 9/1996 | Dreier . |
| 5,558,661 | 9/1996 | Roe et al. . |
| 5,571,096 | 11/1996 | Dobrin et al. . |
| 5,580,411 | 12/1996 | Nease et al. . |
| 5,593,401 | 1/1997 | Sosalla et al. . |
| 5,597,437 | 1/1997 | Lange et al. ............................ 156/260 |
| 5,628,737 | 5/1997 | Dobrin et al. . |
| 5,725,714 | 3/1998 | Fujioka et al. ......................... 156/259 |
| B1 4,636,207 | 11/1989 | Buell . |
| B1 4,662,875 | 4/1989 | Hirotsu et al. . |

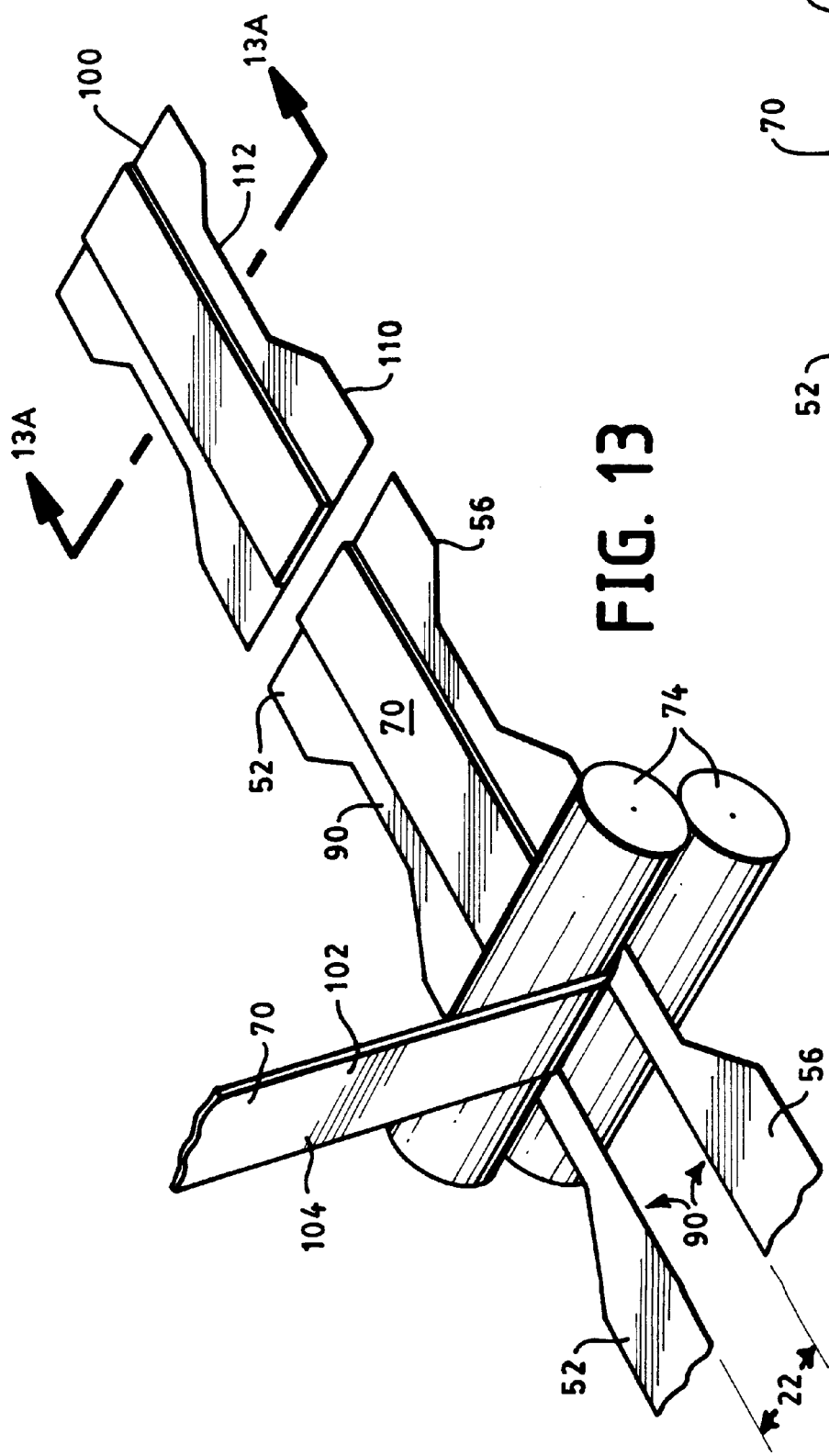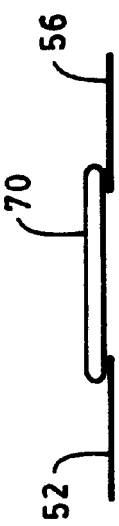

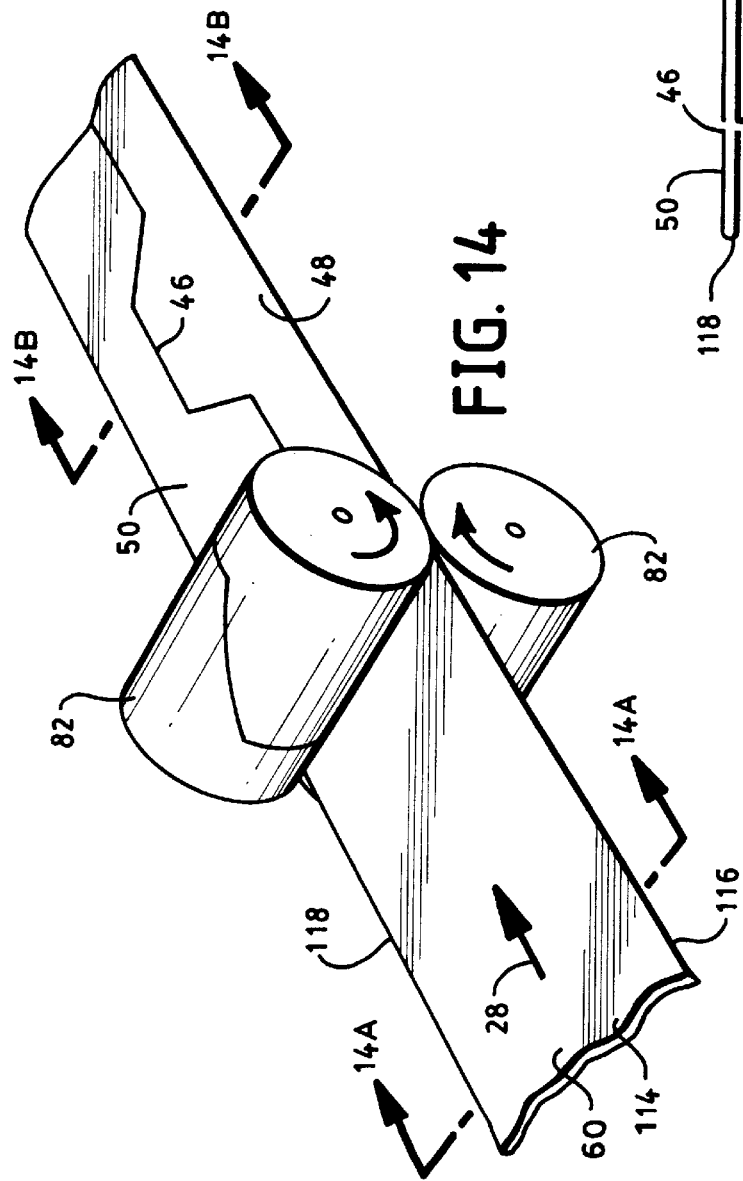

PROCESS FOR MAKING A SHAPED PRODUCT WITH NO MATERIAL WASTE

FIELD OF THE INVENTION

The present invention relates to a method and apparatus for making a shaped article. More particularly, the invention relates to a method and apparatus for more efficiently making a shaped article while reducing the amount of waste material.

BACKGROUND OF THE INVENTION

Conventional articles, such as webs and associated products, have been prepared by forming the web and then cutting away selected portions to form desired shapes and contours at the opposed, lateral sides of the web. Other techniques have included cutting a sheet into two elongated webs so that one edge of each web is straight and the other edge has alternating concave and convex portions. The webs have been affixed to each other or to a water-impervious backing sheet so that the straight edge portions thereof face each other and the alternating concave-convex portions face outwardly.

In further techniques, a concave-convex cutting line has been applied repetitively in a periodical way in the longitudinal direction of a continuous first web to form first and second partial webs. The first partial web has been offset with respect to the second partial web in the longitudinal direction by a prescribed interval so that the concave edges and the convex edges of the first and second partial webs are positioned opposite to and aligned with each. A continuous second web has been used to connect the outside edges opposite to the aligned concave and convex edge portions of the first and second partial webs, and the second web is bonded with the outside edges of the partial webs to form a composite web. Following the bonding, the first and second partial webs of the composite web have been spread apart.

Conventional techniques, such as those described above, have not been able to produce a shaped article having desired contours at sufficiently high speeds and at a sufficient reduction in the amount of wasted of material. In particular, the conventional techniques have been limited to a side contour, repeat pattern in which each individual pattern is longitudinally symmetrical. As a result, the conventional techniques have been unable to efficiently produce a shaped article having side contours with a multi-segment repeating pattern in which the pattern includes two or more different pattern-segments. As a result, the conventional techniques have not been sufficiently able to efficiently produce individual shaped articles which are non-symmetric along their longitudinal, lengthwise directions.

BRIEF DESCRIPTION OF THE INVENTION

The present invention provides a distinctive process for creating a shaped article, such as the representatively shown, shaped web. Generally stated, the technique of the invention includes a pivoting of a first portion of a cooperating web layer substantially about a first joining region to lie laterally adjacent to a first portion of a primary web layer. The cooperating web layer has been positioned in a superposed facing relation with the primary web layer with the primary web layer having a first and second, lateral side edge regions, and the cooperating web layer having third and fourth, lateral side edge regions. The first side edge region of the primary web layer has been synchronized to the third side edge region of the cooperating web layer along the first joining region, and the second side edge region of the primary web layer has been synchronized to the fourth side edge region of the cooperating web layer along a second joining region to provide a synchronized laminated web. The laminated web has been separated along a serpentine division line to provide a first composite web and at least a second composite web. The first composite web has the first portion of the primary web layer combined with the first portion of the cooperating web layer, and the second composite web has a second portion of the primary web layer combined with a second portion of the cooperating web layer.

In a distinctive apparatus aspect of the invention, an apparatus for creating a shaped article can include a positioning mechanism for placing a cooperating web layer in a superposed facing relation with a primary web layer. The primary web layer has first and second lateral side edge regions, and the cooperating web layer has third and fourth lateral side edge regions. A coordinating mechanism synchronizes the first edge region of the primary web layer to the third edge region of the cooperating web layer along a first joining region, and synchronizes the second edge region of the primary web layer to the fourth edge region of the cooperating web layer along a second joining region to form a synchronized laminated web. A partitioning mechanism separates the laminated web along a serpentine division line to provide a first composite web and at least a second composite web. The first composite web has a first portion of the primary web layer combined with a first portion of the cooperating web layer, and the second composite web has a second portion of the primary web layer combined with a second portion of the cooperating web layer. A relocating mechanism pivots the first portion of the cooperating web layer substantially about the first joining region to lie laterally adjacent to the first portion of the primary web layer.

A further aspect of the technique of the invention can include a pivoting of the second portion of the cooperating web layer substantially about the second joining region to lie laterally adjacent to the second portion of the primary web layer.

In its various aspects and configurations, the present invention can produce a desired contoured, shaped article at high speeds and can produce the shaped article with a lateral side contour having a periodically repeating pattern in which each individual repeat pattern section or cycle has at least two different pattern-segments. The present invention can advantageously produce individual shaped articles which are substantially non-symmetric along their longitudinal, lengthwise directions. Thus, the present invention can generate individual shaped articles having longitudinally opposed end sections that are dissimilar and distinctively different, while also reducing the amount of wasted material. In particular aspects, the technique of the invention can produce the desired shaped articles while generating substantially zero waste of selected component webs.

BRIEF DESCRIPTION OF THE DRAWINGS

The present invention will be more fully understood and further advantages will become apparent when reference is made to the following detailed description and accompanying drawings in which:

FIG. 3A representatively shows a lateral cross-sectional view of the contoured web taken along line 3A—3A of FIG. 3;

FIG. 11A representatively shows a cross-sectional view taken along line 11A—11A of FIG. 11;

FIG. 13 representatively shows a configuration of the invention which assembles a supplemental web layer between a portion of the cooperating web layer and a portion of the primary web layer to provide a composite contoured web;

FIG. 13A representatively shows a lateral cross-sectional view of the contoured web taken along line 13A—13A of FIG. 13;

FIG. 14 shows a representative isometric view of a configuration of the invention in which the synchronized laminated web is formed from a tubular member, and the cutter generates the desired serpentine division line to form a pair of substantially seamless composite webs;

FIG. 14A representatively shows a lateral, cross-sectional view of the tubular member;

FIG. 14B representatively shows a lateral, cross-sectional view taken along line 14B—14B of FIG. 14.

DETAILED DESCRIPTION OF THE INVENTION

Figure 1:
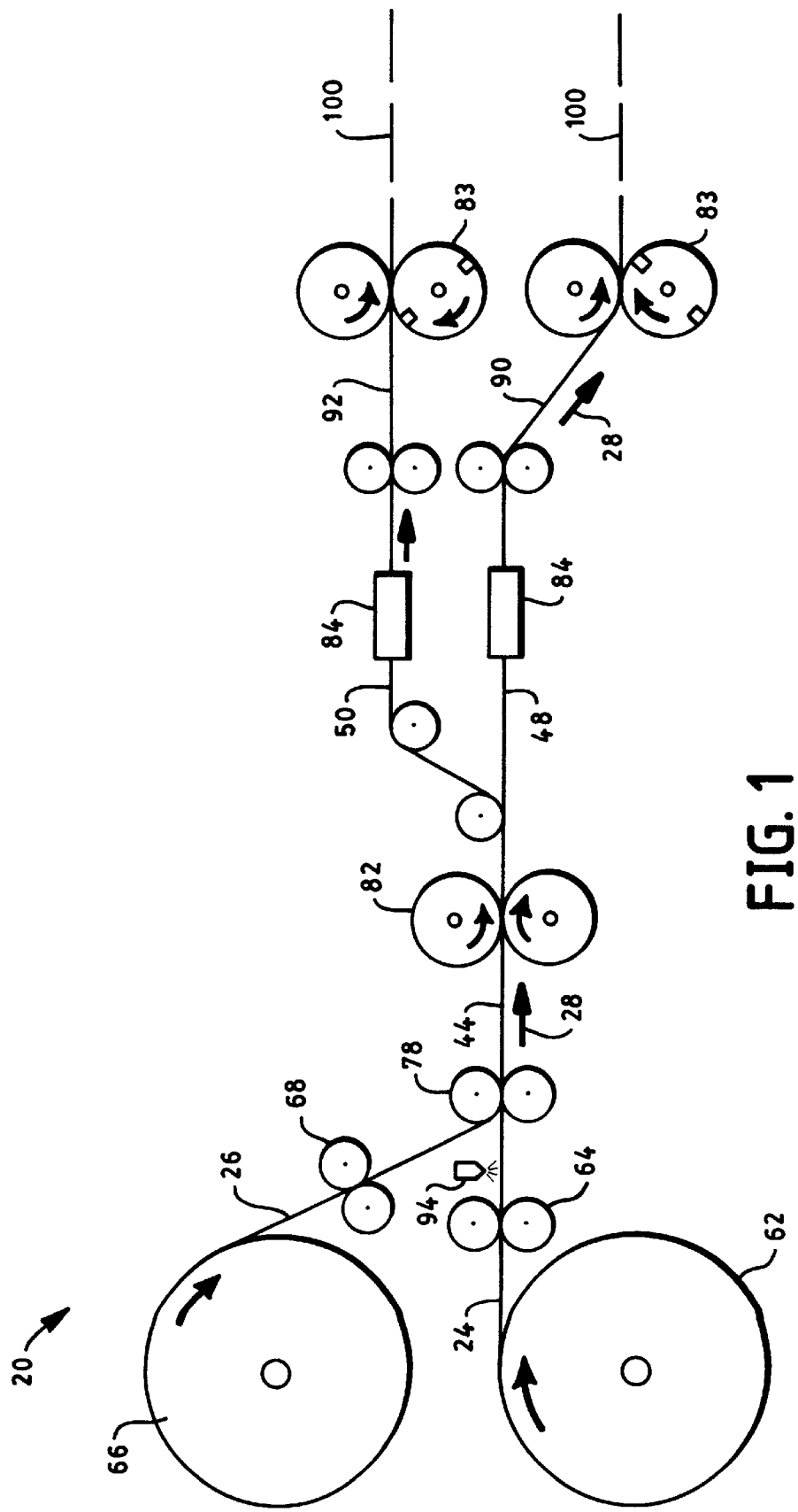
FIG. 1 representatively shows a schematic view of the process and apparatus of the invention.
Figure 2:
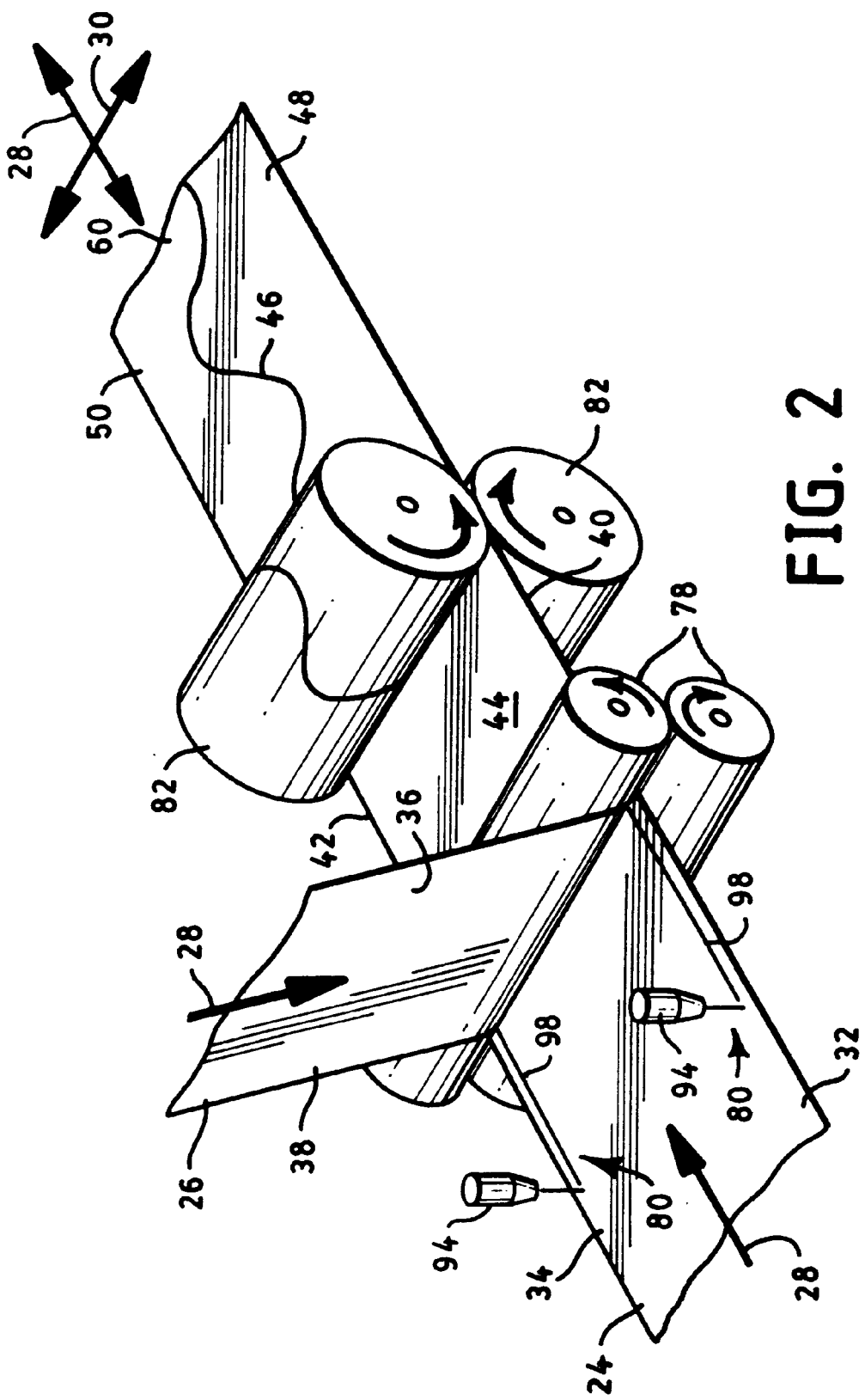
FIG. 2 shows a representative isometric view of the method and apparatus of the invention at the region where the synchronized laminated web is formed with an attachment bond, and where a cutter generates the desired serpentine division line to form a pair of composite webs.
Figure 3:
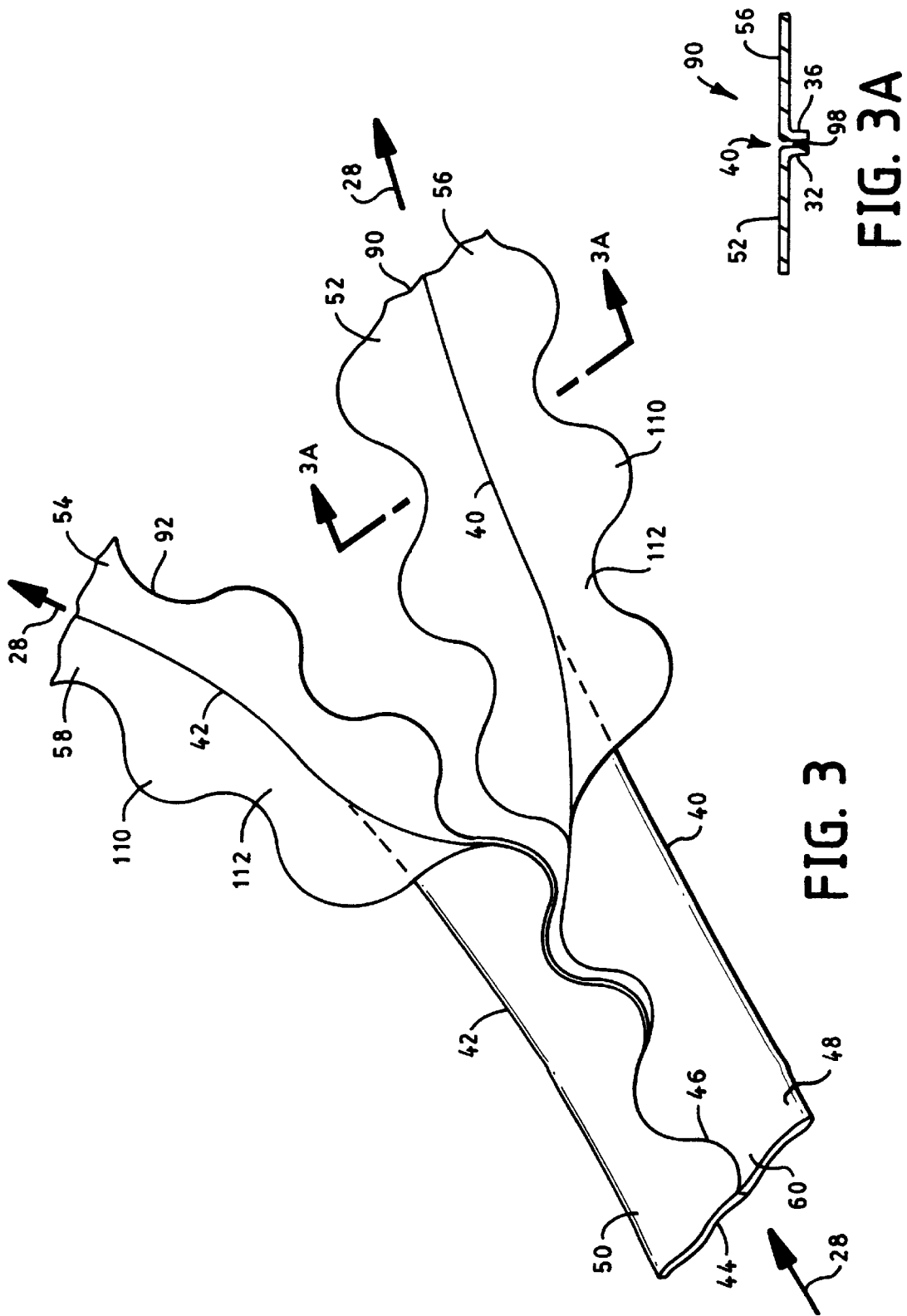
FIG. 3 representatively shows a pivoting and unfolding of the individual composite webs of FIG. 2 to form their corresponding contoured webs.

With reference to FIGS. 1, 2 and 3, a distinctive technique 20 for making a desired shaped article, such as the representatively shown contoured web 90, includes a pivoting of a first portion 56 of a cooperating web layer 26 substantially about a first joining region 40 to lie laterally adjacent to a first portion 52 of a primary web layer 24. The cooperating web layer 26 has been positioned in a superposed facing relation with the primary web layer 24 with the primary web layer 24 having a first and second, lateral side edge regions 32 and 34, and the cooperating web layer 26 having third and fourth, lateral side edge regions 36 and 38. The first side edge region 32 of the primary web layer 24 has been synchronized to the third side edge region 36 of the cooperating web layer 26 along the first joining region 40, and the second side edge region 34 of the primary web layer 24 has been synchronized to the fourth side edge region 38 of the cooperating web layer 26 along a second joining region 42 to provide a synchronized laminated web 44. The laminated web 44 has been separated along a serpentine division line 46 to provide a first composite web 48 and at least a second composite web 50. The first composite web 48 has the first portion 52 of the primary web layer 24 combined with the first portion 56 of the cooperating web layer 26, and the second composite web 50 has a second portion 54 of the primary web layer 24 combined with a second portion 58 of the cooperating web layer 26.

In another aspect of the invention, a pivoting of a second portion 58 of the cooperating web layer 26 about the second joining region 42 can be configured to provide a second contoured web 92. In still other aspects, the technique of the invention can further include a sectioning of the first contoured web into a plurality of individual, shaped articles 100. In a more particular aspect, the technique can divide the first contoured web 90 into a plurality of individual, shaped articles 100 which are longitudinally non-symmetric.

A distinctive apparatus for creating the desired shaped article can include a positioning mechanism, such as provided by directing rollers 78, which places a cooperating web layer 26 in a superposed facing relation with a primary web layer 24. The primary web layer 24 has first and second lateral side edge regions 32 and 34, and the cooperating web layer 26 has third and fourth lateral side edge regions 36 and 38. A coordinating mechanism 80, such as provided by the representatively shown direct attachment bonds 98, synchronizes the first edge region 32 of the primary web layer 24 to the third edge region 36 of the cooperating web layer 26 along a first joining region 40, and synchronizes the second edge region 34 of the primary web layer 24 to the fourth edge region 38 of the cooperating web layer 26 along a second joining region 42 to thereby form a synchronized laminated web 44. A partitioning mechanism, such as provided by a cutter 82, separates the laminated web 44 along a serpentine division line 46 to provide a first composite web 48 and at least a second composite web 50. The first composite web 48 has a first portion 52 of the primary web layer 24 combined with a first portion 56 of the cooperating web layer 26, and the second composite web 50 has a second portion of the primary web layer 24 combined with a second portion 58 of the cooperating web layer 26. A relocating mechanism, such a provided by an unfolding device 84, pivots the first portion 56 of the cooperating web layer 26 substantially about the first joining region 40 to lie laterally adjacent to the first portion 52 of the primary web layer 24 to form a first contoured web 90. Accordingly, the first contoured web can be operatively provided by a cooperating, simultaneously moving, generally adjacent, laterally side-by-side combination of the first portion 56 of the cooperating web layer and the first portion 52 of the primary web layer.

Another aspect of the invention can include a second relocating mechanism which provides a pivoting of the second portion 58 of the cooperating web layer 26 substantially about the second joining region 42 to lie laterally adjacent to the second portion 54 of the primary web layer 24 to form a second contoured web 92. Accordingly, the second contoured web can be operatively provided by a cooperating, simultaneously moving, generally adjacent, side-by-side combination of the second portion 58 of the cooperating web layer and the second portion 54 of the primary web layer.

In further aspects, the invention can include a sectioning mechanism 83 which divides the first and/or second contoured web into a plurality of individual, shaped articles 100. In a more particular aspect, the technique can divide the appointed contoured webs 90 and/or 92 into a plurality of individual, shaped articles 100 which are longitudinally non-symmetric.

It should be noted that portions of the present description may particularly mention the manner in which the various aspects of the invention can be related to the first composite web 48. It should, however, be readily appreciated that the same discussion and description is also intended to apply to the manner in which the various aspects of the invention can be related to the second composite web 50 in an appropriate corresponding context. In addition, the method and apparatus of the invention may be configured to produce individual shaped articles 100 which are substantially symmetrical along their longitudinal lengths with the longitudinally opposed, half-portions of each shaped article substantially being mirror-images of each other. Desirably, the technique of the invention can be configured to produce individual articles 100 which are substantially non-symmetrical along their longitudinal lengths.

It should also be noted that the present description may mention the manner in which the various aspects of the invention can be employed to construct a particular shaped article. It should be appreciated that the present invention can be employed to construct a particular component or subassembly of a more complex article. Accordingly, the contoured webs 90 and 92 or the individual, shaped article 100 may be further assembled to or otherwise combined with other components, as desired. Additionally, it should be appreciated that either or both of the primary web layer 24 and the cooperating web layer 26 may be a composite web, which is composed of a predetermined plurality of sublayers or sub-components, as desired.

With reference to FIG. 1, a suitable transporting mechanism, such as provided by the illustrated system of transport rollers 64, is constructed and arranged to move and direct a substantially continuous primary web layer 24 along an appointed machine-direction 28. The primary web layer is delivered at a predetermined speed from a suitable supply of the primary web layer, such as provided by the illustrated supply roll 62 or other bulk storage accumulation of the material. For the purposes of the present invention, the machine-direction 28 is the direction along which a particular component or material is transported length-wise along and through a particular, local position of the apparatus and method of the invention. In the shown configuration, for example, the primary web layer 24 can be delivered and transported along the apparatus and process toward the location of an operative, attachment-forming device, such as the representatively shown system of adhesive applicators 94.

A conventional web guide mechanism can be employed to control the positioning of the primary web layer 24 along a cross-direction 30 of the process. For the purposes of the present invention, the cross-direction 30 lies generally within the plane of the material being transported through the process and is aligned perpendicular to the local machine-direction 28. Accordingly, in the view of the arrangement representatively shown in FIG. 1, the cross-direction 30 extends perpendicular to the plane of the sheet of the drawing.

The primary web layer 24 may be composed of various materials, such as polymer films, nonwoven fabrics, foam layers, airlaid fibrous webs, bonded-carded webs, through-air-bonded webs, and the like, as well as combination thereof. The primary web layer may be composed of synthetic materials, natural materials, or combinations thereof. In the representatively shown configuration, the primary web layer 24 is composed of a nonwoven fabric. For example, the first web can be a spunbond or other nonwoven fabric which includes synthetic polymer fibers, such as fibers composed of polyethylene, polyester, polypropylene, or combinations thereof. In other configurations, the primary web layer may be composed of airlaid matrix which includes cellulosic fibers.

A suitable transporting mechanism, such as provide by the illustrated system of transport rollers 68, is configured to deliver to move a substantially continuous cooperating web layer 26 along its appointed machine-direction 28. The cooperating web layer is delivered at a predetermined speed from a suitable supply of the cooperating web layer, such as provided by the illustrated supply roll 66 or other bulk storage accumulation of the material. A conventional web guide mechanism can be employed to control the positioning of the primary web layer 24 along a cross-direction 30 of the process.

The cooperating web layer 26 may also be composed of various types of materials, such as polymer films, nonwoven fabrics, foam layers, airlaid fibrous webs, bonded-carded webs, through-air-bonded webs, and the like, as well as combination thereof. In particular aspects of the invention, the process and apparatus can be constructed to provide the primary and/or cooperating web layer in a configuration which is substantially liquid impermeable. In another aspect, the process and apparatus can be arranged to provide the primary and/or cooperating web layer in a configuration which is air permeable and breathable.

A positioning mechanism, such as provided by the shown system of directing rollers 78, operatively locates and transfers the moving, cooperating web layer 26 into a superposed, face-to-face relation with the moving, primary web layer 24. At the location of the process and apparatus where the cooperating web layer 26 and the primary web layer 24 are operatively brought together for further processing, each of the primary web layer and cooperating web layer are substantially continuously directed along the appointed machine-direction 28 of the process and apparatus.

For the purposes of the present invention, an appointed component region is operatively synchronized with another, second component region, when the selected component regions are configured and arranged to move at substantially the same speed and in substantially the same direction. The selected component regions may or may not be in actual physical contact with each other during the synchronized condition. Also, the selected component regions may or may not be affixed to each other during the synchronized condition.

In a particular aspect, the synchronizing of the first edge region 32 of the primary web layer 24 to the third edge region 36 of the cooperating web layer 26 can include an operative attaching of the first edge region 32 to the third edge region 36 along the first adjoining region 40, as representatively shown in FIG. 2. In addition, the synchronizing of the second edge region 34 of the primary web layer 24 with the fourth edge region 38 of the cooperating web layer 26 can include an operative attaching of the second edge region 34 to the fourth edge region 38 along the second joining region 42. In the representatively shown configurations, for example, the first joining region 40 and the second joining region 42 can each extend substantially lengthwise along the machine-direction 28 of the process and apparatus. The attaching operation may provide a substantially direct attachment 98, or an indirect attachment.

With reference to FIG. 2, the synchronizing of the first edge region 32 of the primary web layer to the third edge region 36 of the cooperating web layer with the direct attachment 98 can include a first, substantially permanent affixing of the first edge region to the third edge region along the first adjoining region 40. Alternatively, the synchronizing of the first edge region 32 of the primary web layer with the third edge region 36 of the cooperating web layer can include a temporary attaching of the first edge region to the third edge region along the first adjoining region 40.

Similarly, the synchronizing of the second edge region 34 of the primary web layer to the fourth edge region 38 of the cooperating web layer with the direct attachment 98 can include a second, substantially permanent affixing of the second edge region to the fourth edge region along the second joining region 42. Alternatively, the synchronizing of the second edge region 34 of the primary web layer with the fourth edge region 38 of the cooperating web layer can include a temporary attaching of the second edge region to the fourth edge region along the second joining region 42.

The arrangement and configuration of the direct attaching mechanism may be substantially continuous, or may be intermittent with a regular or irregular pattern, as desired. In addition, the attaching mechanism may be of any operative type, such as adhesive bonds, thermal bonds, sonic bonds, welds, pins, staples, sewing, stitching and the like, as well as combinations thereof. In the illustrated arrangement, for example, the attaching mechanism includes the adhesive bonds 80 formed through the operation of the shown adhesive applicators 94.

Various types of conventional applicating or depositing techniques can be employed to deliver the selected adhesive to form the synchronized laminated web 44. For example, air-depositing techniques such as spraying, meltblowing, swirling or the like, as well as combinations thereof, can be employed. Alternately, various contact techniques, such as slot, bead, or gravure coating of adhesive onto the substrates, may be employed.

Figure 4:
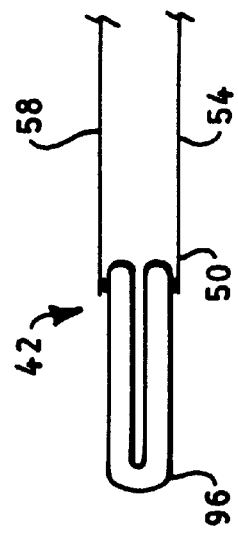
FIG. 4 representatively shows a connector member which is interposed between a side edge region of the primary web layer and a side edge region of the cooperating web layer along their corresponding joining region to synchronize of the edge region of the primary web layer to the edge region of the cooperating web layer with an indirect attachment.
Figure 5:
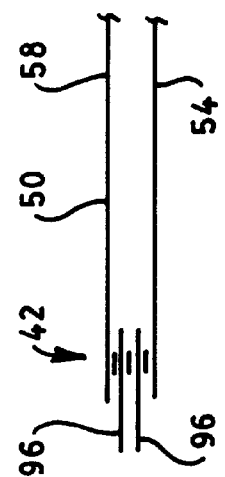
FIG. 5 representatively shows an expanded view of another system of connector members which are interposed between a side edge region of the primary web layer and a side edge region of the cooperating web layer along their corresponding joining region to synchronize of the edge region of the primary web layer to the edge region of the cooperating web layer with an indirect attachment.
Figure 4A:
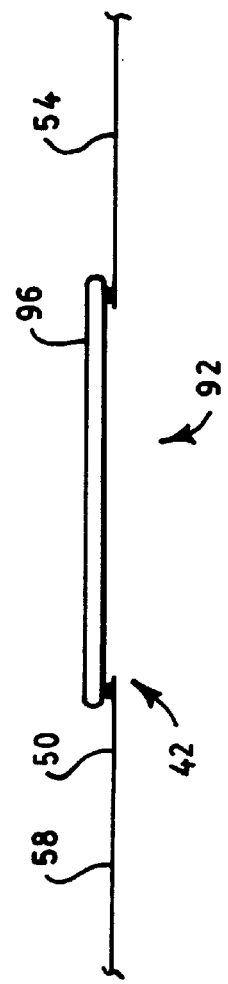
FIG. 4A representatively shows a lateral cross-sectional view of the joining region of the resultant contoured web after a portion of the cooperating web layer has been pivoted about the joining region of FIG. 4 to dispose the connector member between the attached portions of the primary and cooperating web layers.
Figure 5A:
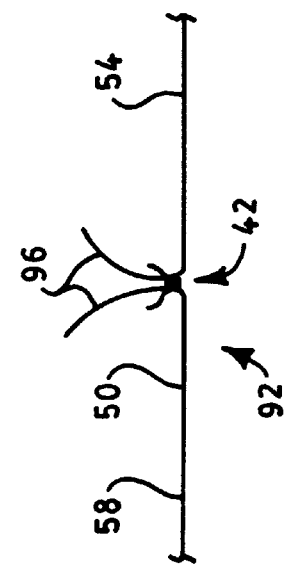
FIG. 5A representatively shows a lateral cross-sectional view of the joining region of the resultant contoured web after a portion of the cooperating web layer has been pivoted about the joining region of FIG. 5 to dispose the connector members between the attached portions of the primary and cooperating web layers.

With reference to FIGS. 4 through 5A, the synchronizing of the first edge region 32 of the primary web layer to the third edge region 36 of the cooperating web layer with an indirect attachment may, for example, include at least one separately provided, connector member 96 which is interposed between the first side edge region 32 of the primary web layer and the third side edge region 36 of the cooperating web layer along the first joining region 40. Similarly, another separately provided, connector member 96 may be interposed between the second side edge region 34 of the primary web layer and the fourth side edge region 38 of the cooperating web layer along the second joining region 42. Each of the connector members extends lengthwise substantially in the machine-direction 28 along its corresponding joining region 40 or 42, and may be of equal or unequal size along their cross-direction 30. The connector members may extend lengthwise in a discontinuous or substantially continuous configuration, as desired, to provide the synchronized laminated web 44. In the arrangement of FIG. 4, for example, the connector member 96 may be folded into a C-shape which is convex in the laterally outboard direction.

Figure 6:
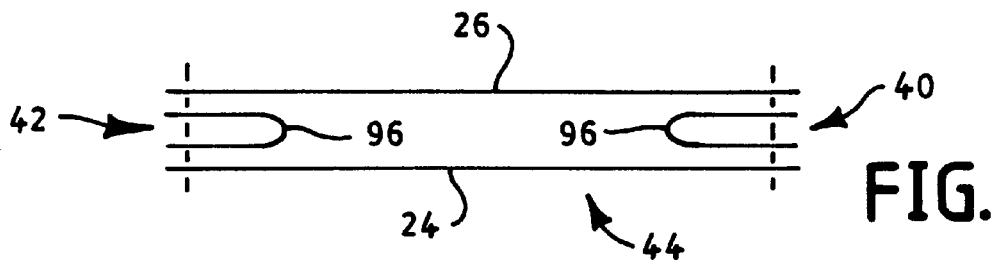
FIG. 6 representatively shows a system connector members which are folded into a C-shape which is concave in the laterally outboard direction, and are located at each of the appointed joining regions.
Figure 6A:
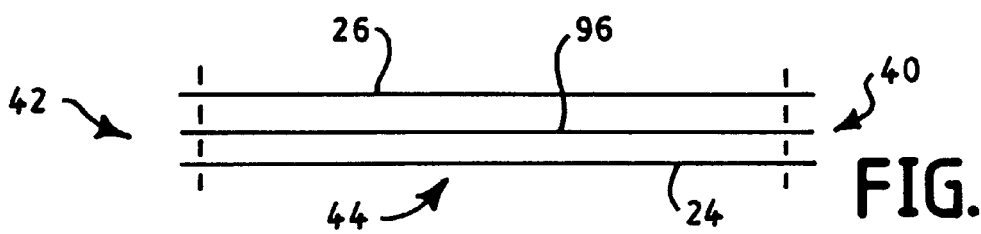
FIG. 6A representatively shows a unitary connector member which extends across the cross-directional width of the synchronized web, and is located at both of the joining regions.
Figure 6B:
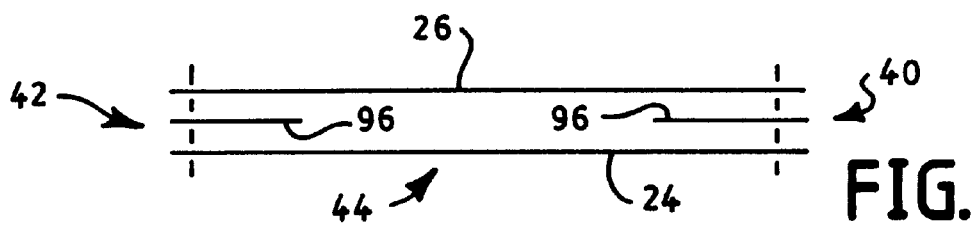
FIG. 6B representatively shows a single, separately provided connector member located at each joining region, with each connector member having the form of a sheet layer arranged substantially parallel to the primary and cooperating web layers.
Figure 6C:
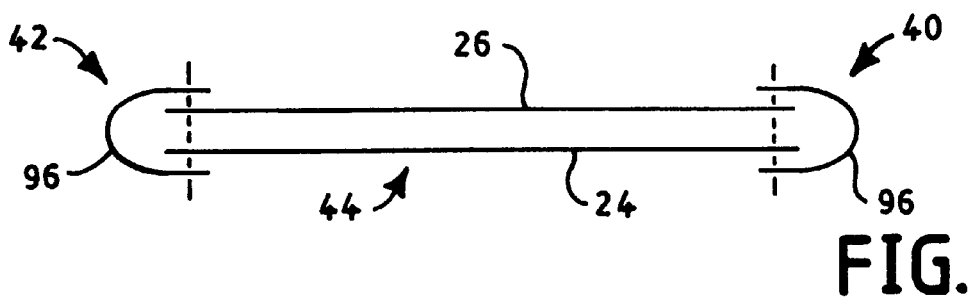
FIG. 6C representatively shows a system of connector members which are folded into a C-shape which is convex in the laterally outboard direction, and are attached to the outward-side surfaces of the primary and cooperating web layers at their corresponding joining regions.

Examples of other configurations of the connector member 96 are representatively shown in FIGS. 6 through 6C. More particularly, FIG. 6 representatively shows a pair of connector members 96 which are folded into a C-shape which is concave in the laterally outboard direction, and are located at each of the joining regions 40 and 42. Additionally, the C-shape connector member is joined to inward side surfaces of the corresponding portions of the primary web layer and cooperating web layer. FIG. 6A representatively shows a one-piece, unitary connector member which extends across the cross-directional width of the synchronized web 44 and is located at both of the joining regions 40 and 42. FIG. 6B representatively shows a pair of separately provided connector members, one of which is located at each joining region. Each connector member has the form of a sheet layer arranged substantially parallel to the primary and cooperating web layers 24 and 26. FIG. 6C representatively shows another pair of connector members 96 which are folded into a C-shape and are convex in the laterally outboard direction. Each folded connector member is attached to the outward-side surfaces of the primary and cooperating web layers 24 and 26 at its corresponding joining region 40 or 42.

Figure 7:
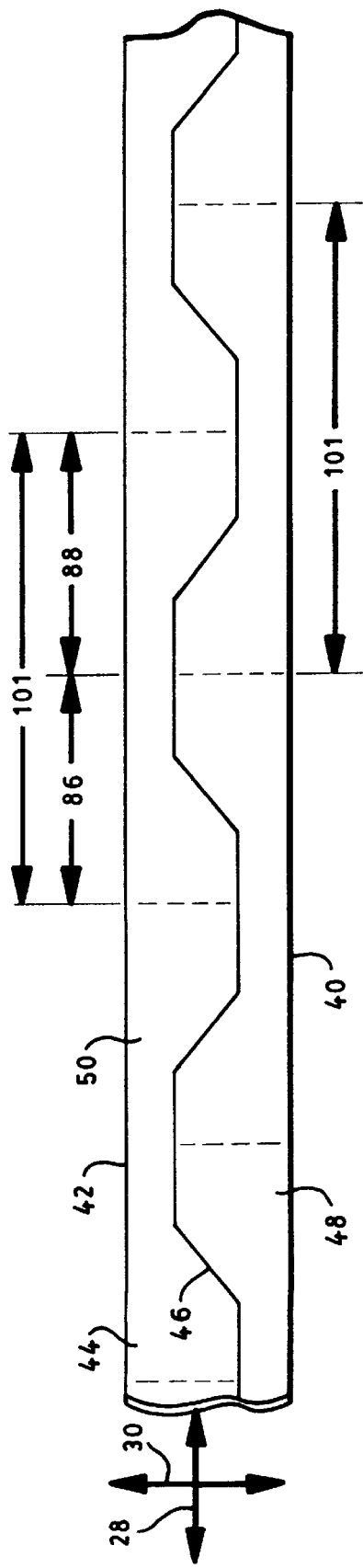
FIG. 7 representatively shows a schematic top view of a representative serpentine division line which provides a longitudinally repeating pattern with pattern segments which are substantially symmetrical along their longitudinal, machine-direction lengths.
Figure 8:
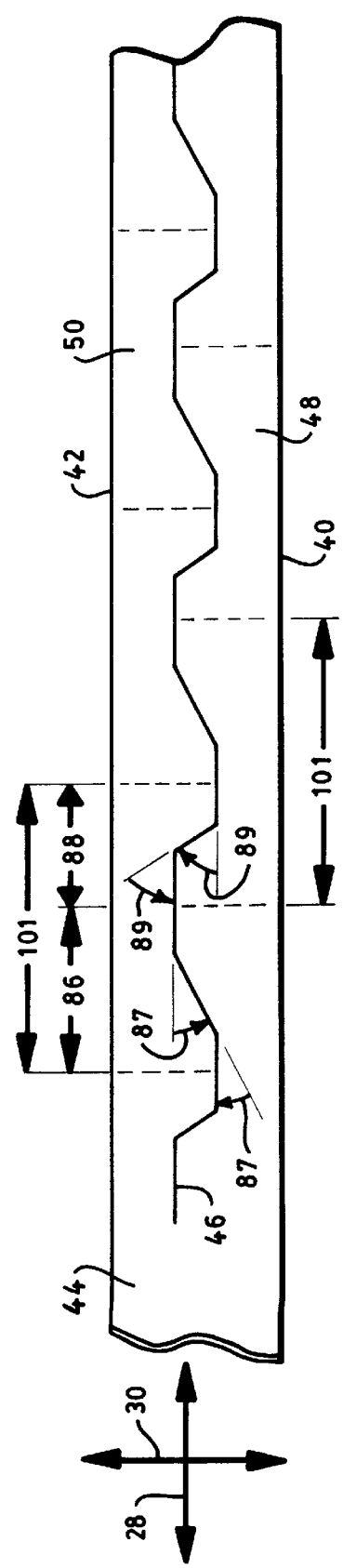
FIG. 8 representatively shows a schematic top view of a representative serpentine division line which provides a longitudinally repeating pattern with pattern segments which are substantially non-symmetrical along their longitudinal, machine-direction lengths.

With reference again to FIGS. 1, 2 and 3, a selected partitioning mechanism 82 may separate the laminated web 44 along a serpentine division line 46 which extends longitudinally in the machine-direction 28 along an appointed medial section 60 of the laminated web 44, and undulates laterally side-to-side with a cyclical, periodically repeating pattern. The repeating pattern provides a first pattern segment 86, and a cross-directionally opposed, second pattern segment 88, which undulates back and forth in a substantially regular, cyclically repeating pattern. The partitioning mechanism can be provided by the illustrated cutter 82. Suitable cutter mechanisms can include die cutters, water cutters, laser cutters or other energy-beam cutters, and the like, as well as combinations thereof. The serpentine division line may be continuously curvilinear, or may be composed of an interconnected series of individual straight line portions, or individual curved line portions, as well as combinations thereof.

Where the technique of the invention is configured to provide individual shaped articles 100, the synchronized web 44 can define an interconnected plurality of article lengths 101 along the machine-direction 28, as representatively shown in FIGS. 7 and 8. More particularly, FIG. 7 representatively shows a configuration in which the individual shaped articles 100 are intended to have a longitudinal symmetry (with substantially matching plan forms at the opposed, longitudinal ends of the article). In the arrangement of FIG. 7, the repeating pattern of the serpentine division line 46 can provide a first pattern segment 86, and a longitudinally adjacent second pattern segment 88. The second pattern segment 88 has a longitudinally mirrored-symmetry relative to the first pattern segment 86. Thus, when observing the individual length dimensions of the two pattern segments along the same machine-direction, the second pattern segment 88 is observed to be substantially identical to the first pattern segment 86, but is observed to be "flipped" length-wise, in manner which provides the arrangement of a length-wise, substantially mirror-image configuration, as compared to the first pattern segment.

With reference to FIG. 8, another aspect of the invention can be configured to provide the shaped article with a desired non-symmetry along the longitudinal, machine-direction. To provide the longitudinal asymmetry, the partitioning mechanism can be configured to separate the laminated web 44 along a distinctive, variegated, serpentine division line 46. The multi-section, variegated division line 46 extends longitudinally in the machine-direction 28 along the appointed medial section 60 of the laminated web 44, and undulates laterally side-to-side with a cyclical, periodically repeating pattern. The repeating pattern provides a first pattern segment 86, and a longitudinally adjacent, second pattern segment 88. The second pattern segment is dissimilar from the first pattern segment, and is longitudinally non-symmetric with the first pattern segment.

The first pattern-segment 86 of the selected variegated pattern has a first back-and-forth switch-back configuration which traverses through a first angle 87, and the second pattern-segment 88 of the selected variegated pattern has a second back-and-forth switch-back configuration which traverses through a second angle 89. The second switch-back angle differs from the first switch-back angle, and may be relatively greater than or less than the first switch-back angle. As a result, the variegated division line 46 can advantageously provide for the production of individual, shaped articles 100 having a pair of longitudinally opposed end portions which differ from each other.

Figure 9:
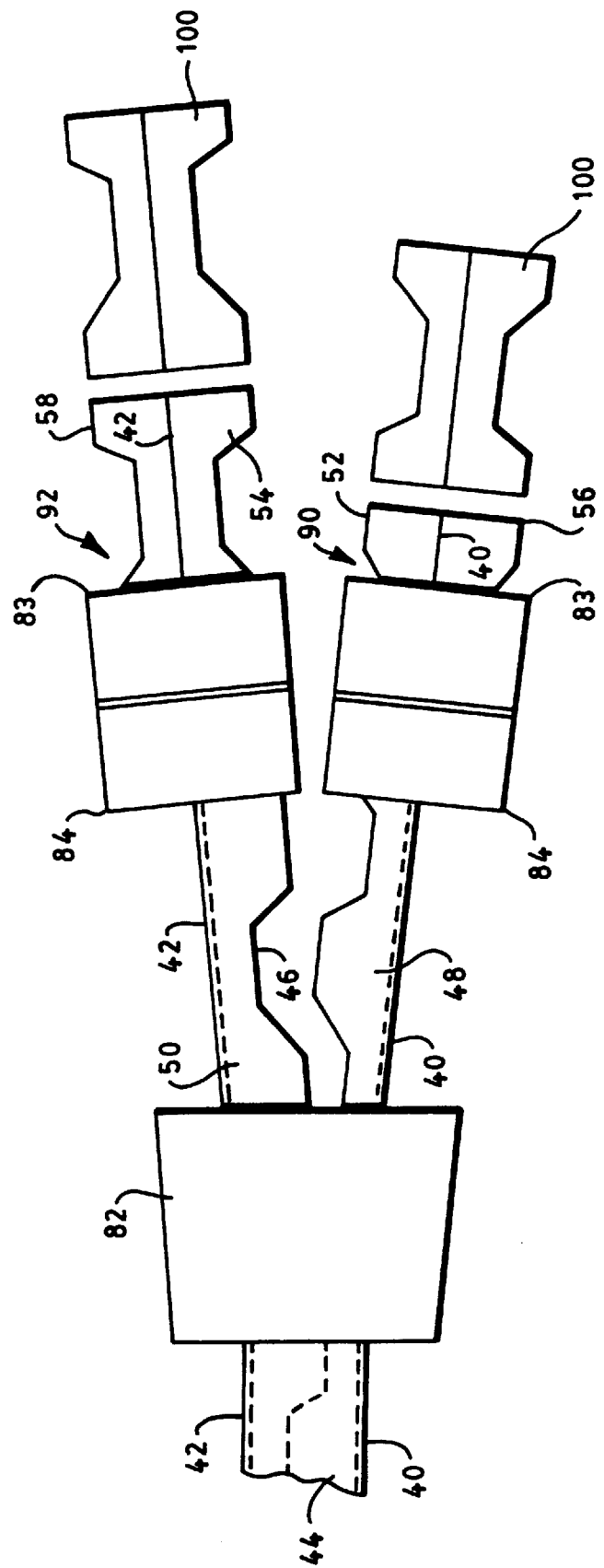
FIG. 9 representatively shows the operation of a relocating mechanism which provides the desired pivoting about the appointed joining regions, and the operation of a sectioning mechanism which divides the contoured web into a plurality of shaped articles.

With reference to FIGS. 1 and 9, the various configurations of the invention can include a suitable relocating mechanism 84 which can operatively pivot either or both of the first and second portions 56 and 58 of the cooperating web layer 26 about the first and second joining regions 40 and 42, respectively. Equivalently, the relocating mechanism may pivot either or both of the first and second portions 52 and 54 of the primary web layer 24 about the first and second joining regions 40 and 42, respectively. The relocating mechanism 84 can, for example, be provided by a folding board, an unfolding board, an air jet system which blows open the first and second portions, a vacuum system which draws open the first and second portions, or the like, as well as combinations thereof.

In a particular aspect of the invention, the pivoting of the first portion 56 of the cooperating web layer 26 about the first joining region 40 to lie laterally adjacent to the first portion 52 of the primary web layer 24 is configured to provide the first contoured web 90 with bilateral symmetry in the cross-direction 30. Similarly, the pivoting of the second portion 58 of the cooperating web layer 26 about the second joining region 42 to lie laterally adjacent to the second portion 54 of the primary web layer 24 can be configured to provide the second contoured web 92 with bilateral symmetry.

Additionally, the pivoting of the first portion 56 of the cooperating web layer 26 about the first joining region 40 can be configured to provide the first contoured web 90 with a predetermined longitudinal variation along the machine-direction 28. Similarly, the pivoting of the second portion 58 of the cooperating web layer 26 about the second joining region 42 can be configured to provide the second contoured web 92 with the desired, predetermined longitudinal variation. Desirably, the lengthwise longitudinal variation can directly correspond with the at least two different pattern-segments 86 and 88 provided in the repeating pattern of the previously described, variegated serpentine division line 46.

Figure 10:
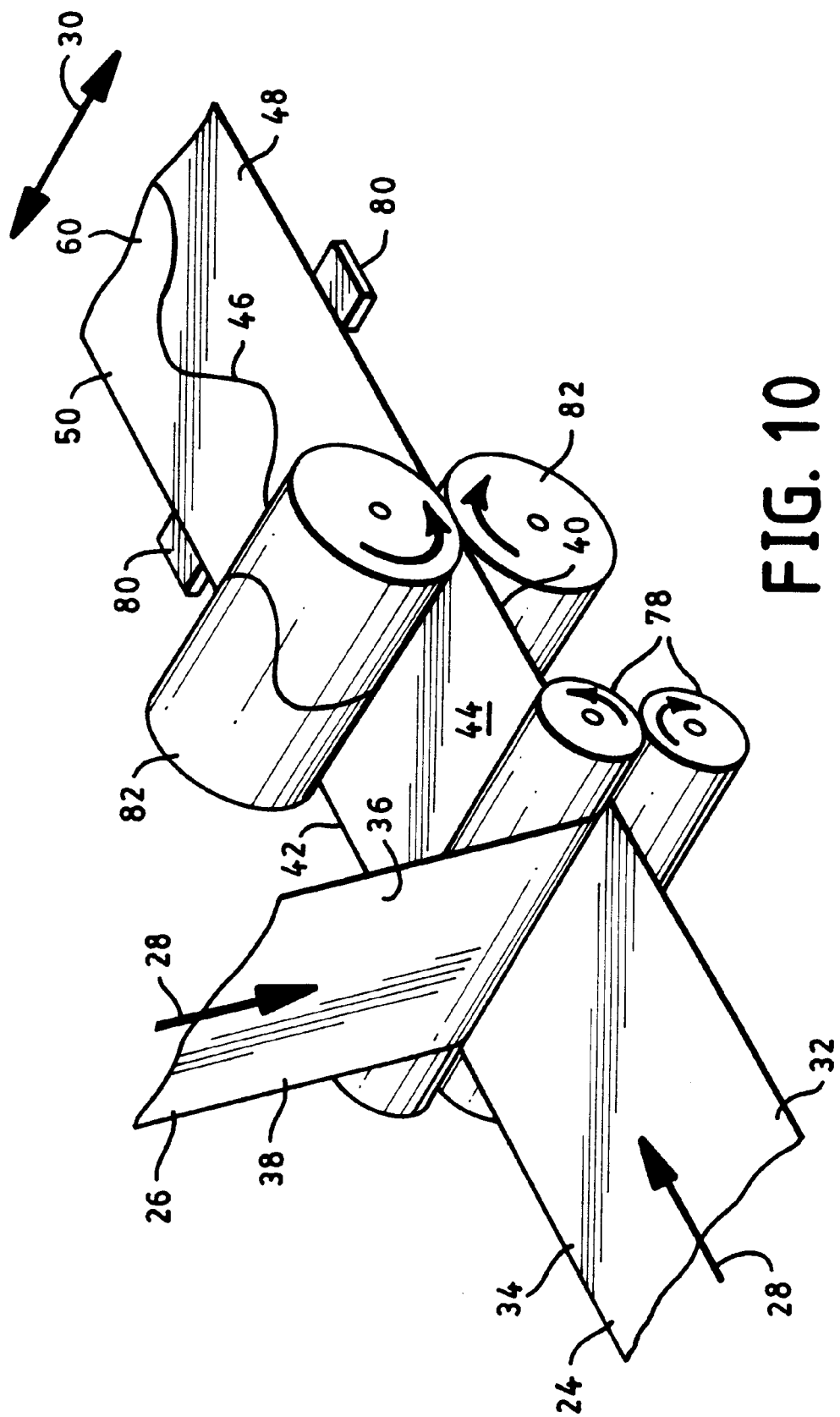
FIG. 10 representatively shows an isometric view of a configuration which synchronizes the primary and cooperating web layers without a direct or indirect affixing of the primary web layer to the cooperating web layer, and which employs a cutter to generate the desired serpentine division line.
Figure 11:
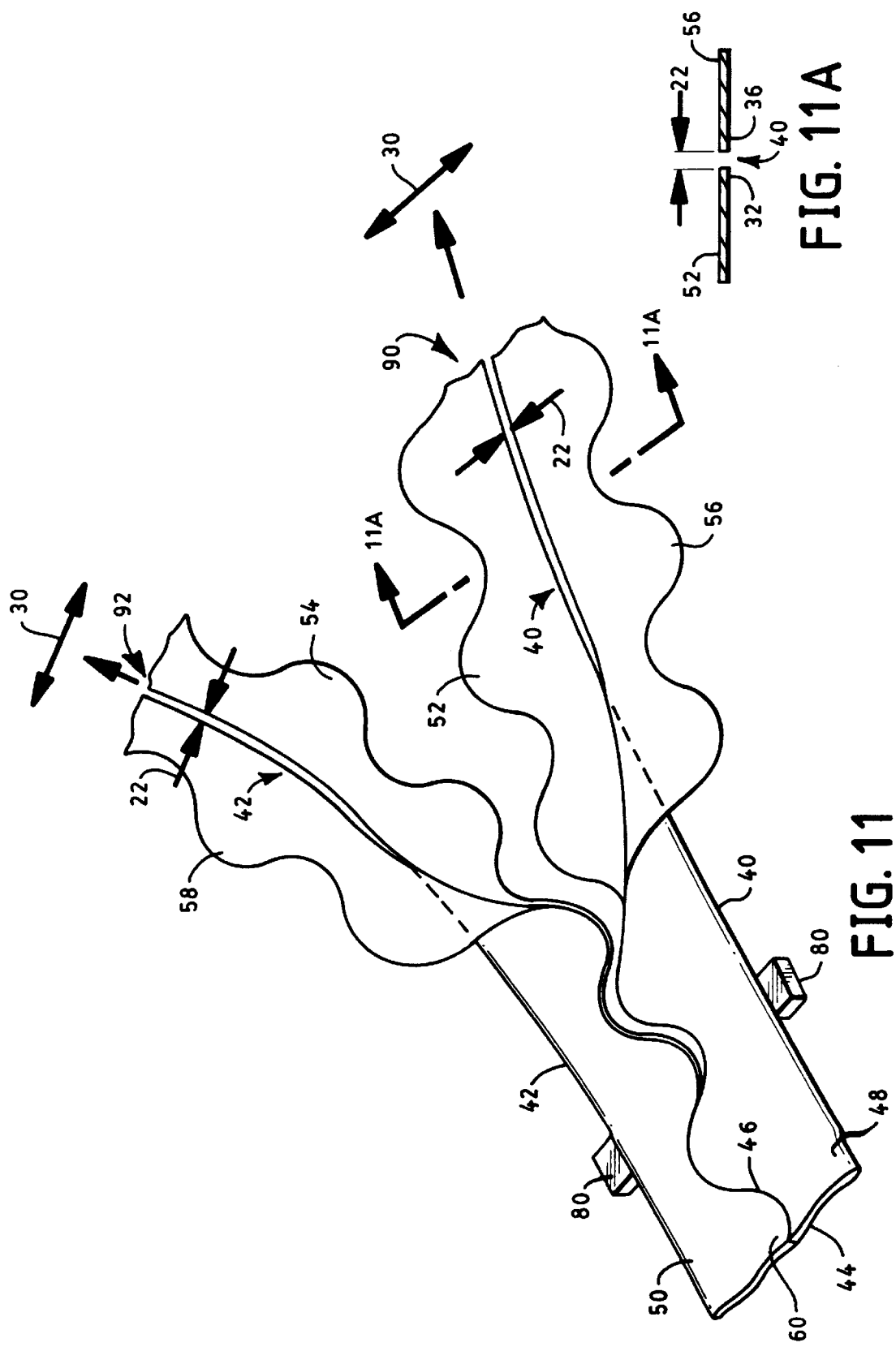
FIG. 11 representatively shows a pivoting and unfolding of the individual composite webs of FIG. 10 to form their corresponding contoured webs.

The process and apparatus of the invention may provide a synchronizing of the primary and cooperating web layers 24 and 26 without a direct or indirect affixing of the primary web layer to the cooperating web layer, as illustrated in FIG. 10. Accordingly, the coordinating mechanism 80 operatively holds the primary web layer and the cooperating web layer along the joining regions 40 and 42 in a manner which operatively maintains the desired simultaneous movement with substantially the same speed and direction. Suitable coordinating mechanisms can, for example, include nipping roller pairs, moving clamps, air jets, pneumatic pressuring devices, vacuum suction devices, devices that produce electrostatic attraction, devices that produce magnetic attraction and the like, as well as combinations thereof. The example arrangement of FIG. 10 shows a representative isometric view of a configuration of the invention in which the synchronized laminated web is formed without an attachment bond, and a rotary die cutter provides the partitioning mechanism 82 which generates the desired serpentine division line 46 to form another pair of composite webs 48 and 50. FIG. 11 representatively shows the pivoting and unfolding of the resultant, individual composite webs from FIG. 10 to form their corresponding contoured webs 90 and 92.

The technique of the invention may further provide a lateral spacing of the first portion 56 of the cooperating web layer 26 away from the first portion 52 of the primary web layer 24 by a discrete spacing distance 22 along the cross-direction 30, as representatively shown in FIGS. 10 through 11A. Similarly, the invention may provide a lateral spacing of the second portion 58 of the cooperating web layer 26 away from the second portion 54 of the primary web layer 24 by a discrete spacing distance 22 along their appropriately corresponding cross-direction 30.

Figure 12:
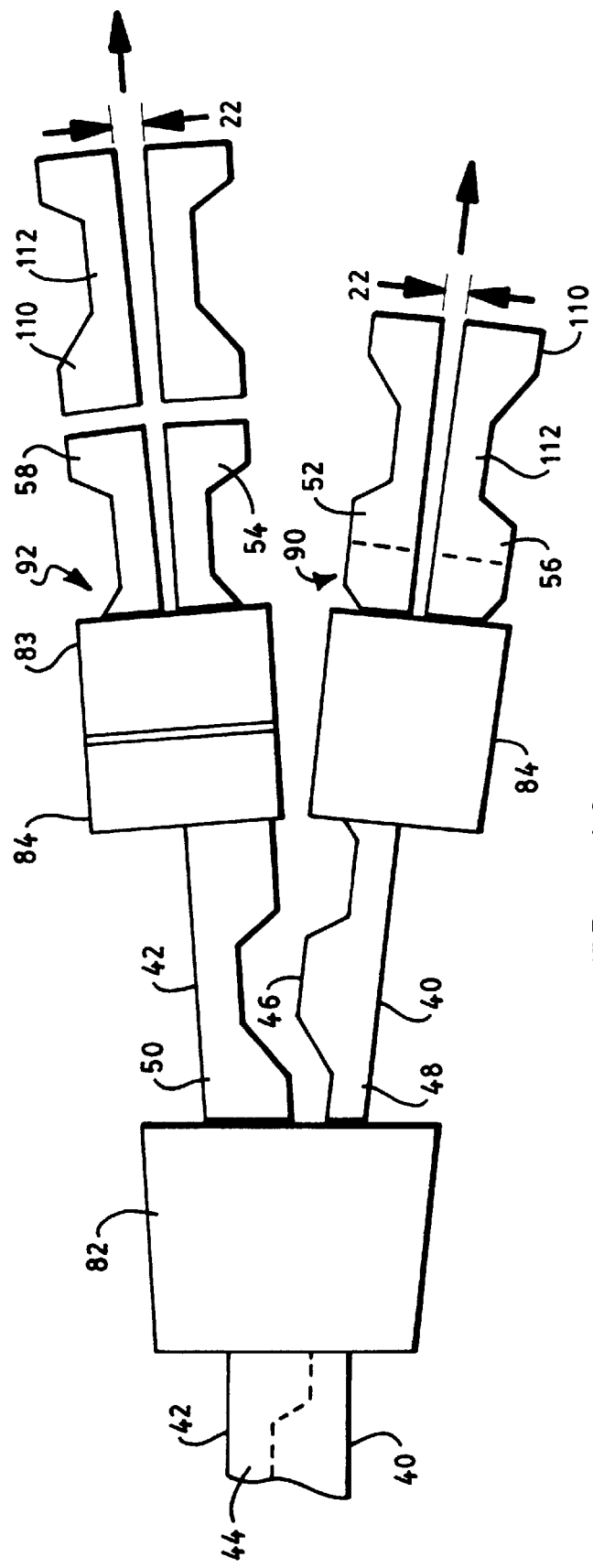
FIG. 12 representatively shows a schematic view of contoured webs in which the associated portions of the primary and cooperating web layers are space apart by a selected distance along the lateral cross-direction.

As illustrated in FIG. 12, the lateral spacing distance 22 can be introduced after the relocating mechanism 84 has pivoted the first portion 56 of the cooperating web layer 26 about the first joining region 40 of the primary web layer 24, or after the relocating mechanism has pivoted the second portion 58 of the cooperating web layer 26 about the first joining region 42 of the primary web layer 24, as the case may be. The sectioning mechanism 83 may or may not be employed at this stage to divide the contoured webs 90 and 92 into individual shaped articles.

In a further aspect of the invention, a selected contoured web can be further processed prior to any cross-directional sectioning operation. As representatively shown in FIGS. 13 and 13A, for example, the contoured web 90 can be delivered to an assembly mechanism, such as the mechanism provided by a system of the illustrated assembly rollers 74. At the assembly rollers, a separately provided first supplemental layer 70 can be placed at an intermediate location interposed between the first portion 56 of the cooperating web layer and the first portion 52 of the primary web layer. The first supplemental web layer 70 has a pair of laterally opposed side edge regions 102 and 104 which extend length-wise along the appointed machine-direction 28. The first portion 56 of the cooperating web layer 26 may or may not be attached or otherwise joined to one side edge region 102 of the first supplemental web layer 70, and the first portion 52 of the primary web layer 24 may or may not be attached or otherwise joined to another side edge region 104 of the first supplemental web layer to provide a first, composite contoured web 90.

Similarly, the second portion 58 of the cooperating web layer 26 may be laterally spaced away from the second portion 54 of the primary web layer 24 by its associated spacing distance 22 along the cross-direction 30, and another, separately provided supplemental layer 70 can be placed at an intermediate location interposed between the second portion 58 of the cooperating web layer and the second portion 54 of the primary web layer. The second portion 58 of the cooperating web layer 26 may or may not be attached to its corresponding side edge region of the second supplemental web layer 72, and the second portion 54 of the primary web layer 24 may or may not be attached to its corresponding side edge region of the second supplemental web layer to provide a second, composite contoured web 92.

As illustrated in FIGS. 3, 12 and 13, each contoured web article 90 and/or 92 can have a plurality of alternating, convex outboard regions 110 and concave outboard regions 112. Additionally, in the various configurations of the invention, each contoured web article 90 and/or 92 can be divided with the selected sectioning mechanism 83 along its associated cross-direction 30 to provide a plurality of individual shaped articles 100. Desirably, the contoured web is cross-directionally divided of at a plurality of said convex outboard regions 110 to provide the plurality of individual, shaped articles. In other desired aspects, each of the individual shaped articles 100 can be longitudinally non-symmetric along their lengthwise, machine-direction 28 (e.g. FIGS. 12 and 13).

The sectioning mechanism 83 can be provided by the illustrated rotary cutters. Suitable cutter mechanisms can also include die cutters, water cutters, laser cutters or other energy-beam cutters, and the like, as well as combinations thereof.

With reference to FIGS. 14 through 14B, the appointed primary web layer and the appointed cooperating web layer can be simultaneously provided by a tubular member 114 composed of a selected material. The tubular member can be operatively flattened to provide the synchronized laminated web 44. The flattened member has a pair of laterally opposed, folded side edge regions 116 and 118 which correspond to the previously described first and second joining regions of the laminated web 44. In desired arrangements, the folded edges are substantially seamless. The flattened member can be separated along the serpentine division line 46 of the invention to provide the first composite web 48 and the second composite web 50. The first composite web has a first, top portion of the tubular member 114 combined with a first bottom portion of the tubular member. Similarly, the second composite web has a second, top portion of the tubular member 114 combined with a second, bottom portion of the tubular member.

Figure 15:
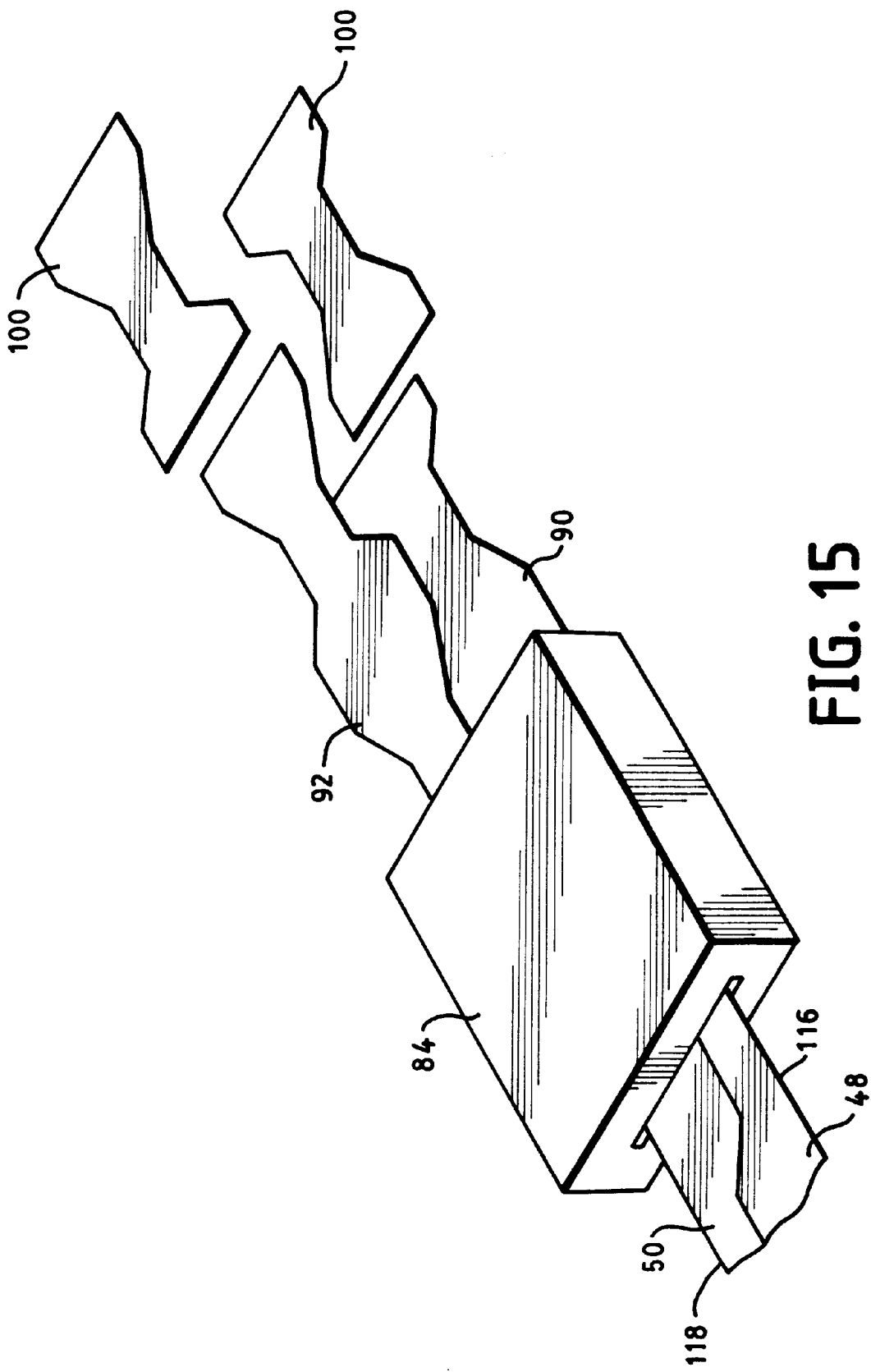
FIG. 15 representatively shows a pivoting of the top portions of the composite webs from FIG. 14 about the folded edge regions to lie laterally adjacent to the bottom portions of the composite webs to form contoured webs, and a dividing of the contoured webs along their cross-directions to form individual shaped articles.

With reference to FIG. 15, the first top portion of the first composite web 48 can be pivoted substantially about the first folded edge region 116 to lie laterally adjacent to the first bottom portion of the first composite web to form the first contoured web 90. Similarly, second, top portion of the second composite web 50 can be pivoted substantially about the second folded edge region 118 to lie laterally adjacent to said second bottom portion of the second composite web to form the second contoured web 92. Thereafter, the contoured webs may be divided along their cross-directions to provide individual shaped articles having the shapes previously described.

The aspect of the invention which employs the tubular member 114 can provide the contoured webs 90 and 92 in a configuration which does not have a longitudinally extending seam along the medial portions of the contoured webs. Similarly, the incorporation of the tubular member can provide the individually shaped articles 100 with a configuration which does not have a lengthwise extending seam along the medial portions of the individual shaped articles.

Having described the invention in rather full detail, it will be readily apparent that various changes and modifications can be made without the parting from the spirit of the invention. All of such changes and modification are contemplated as being within the scope of the invention as defined by the subjoined claims.

I claim:

1. A process for creating a shaped article, comprising a pivoting of a first portion of a cooperating web layer substantially about a first joining region to lie laterally adjacent to a first portion of a primary web layer; wherein
   said cooperating web layer has been positioned in a superposed facing relation with said primary web layer, said primary web layer having first and second, lateral side edge regions, and said cooperating web layer having third and fourth, lateral side edge regions;
   said first edge region of the primary web layer has been synchronized to said third edge region of said cooperating web layer along said first joining region, and said second edge region of the primary web layer has been synchronized to said fourth edge region of said cooperating web layer along a second joining region to provide a synchronized laminated web; and said laminated web has been separated along a serpentine division line to provide a first composite web and at least a second composite web, said first composite web having said first portion of the primary web layer combined with said first portion of the cooperating web layer, and said second composite web having a second portion of the primary web layer combined with a second portion of the cooperating web layer.

2. The process as recited in claim 1, further comprising a pivoting of said second portion of the cooperating web layer about said second joining region to lie laterally adjacent to said second portion of the primary web layer.

3. The process as recited in claim 1, wherein said laminated web has been separated along a serpentine division line which has extended longitudinally along an appointed medial section of the laminated web and has undulated laterally with a periodically repeating pattern, and wherein said repeating pattern has included at least two different pattern-segments.

4. The process as recited in claim 1, wherein said pivoting of said first portion of the cooperating web layer about said first joining region to lie laterally adjacent to said first portion of the primary web layer is configured to provide a first contoured web with bilateral symmetry.

5. The process as recited in claim 1, wherein said pivoting of said first portion of the cooperating web layer about said first joining region to lie laterally adjacent to said first portion of the primary web layer is configured to provide a first contoured web which has a predetermined longitudinal variation.

6. The process as recited in claim 1, wherein said pivoting of said first portion of the cooperating web layer about said first joining region to lie laterally adjacent to said first portion of the primary web layer is configured to provide a first contoured web having a plurality of alternating, convex and concave, outboard regions; and wherein said process further comprises a cross-directional sectioning of said first contoured web at a plurality of said convex outboard regions to provide a plurality of individual, shaped articles.

7. The process as recited in claim 6, wherein said sectioning of said first contoured web into a plurality of individual articles provides individual, shaped articles which are longitudinally non-symmetric.

8. The process as recited in claim 1, wherein said first edge region of the primary web layer has been synchronized to said third edge region of said cooperating web layer by a first attaching of said first edge region to said third edge region along said first joining region, and said second edge region of the primary web layer has been synchronized to said fourth edge region of said cooperating web layer by a second attaching of said second edge region to said fourth edge region layer along said second joining region.

9. The process as recited in claim 1, wherein said first edge region of the primary web layer has been synchronized to said third edge region of said cooperating web layer by a first direct attaching of said first edge region to said third edge region along said first joining region, and said second edge region of the primary web layer has been synchronized to said fourth edge region of said cooperating web layer by a second direct attaching of said second edge region to said fourth edge region along said second joining region.

10. The process as recited in claim 1, wherein said first edge region of the primary web layer has been synchronized to said third edge region of said cooperating web layer by a first indirect attaching of said first edge region to said third edge region along said first joining region, and said second edge region of the primary web layer has been synchronized to said fourth edge region of said cooperating web layer by a second indirect attaching of said second edge region to said fourth edge region along said second joining region.

11. The process as recited in claim 10, wherein said providing of said first indirect attachment assembly of said first edge region of the primary web layer to said third edge region of said cooperating web layer has included an assembling of at least one separately provided connector member between said first edge region and said third edge region along said first joining region; and said providing of said second indirect attachment assembly of said second edge region of the primary web layer to said fourth edge region of said cooperating web layer has included an assembling of another separately provided connector member between said second edge region and said fourth edge region along said first joining region.

12. The process as recited in claim 1, wherein said first edge region of the primary web layer has been synchronized to said third edge region of said cooperating web layer by a first, substantially permanent affixing of said first edge region to said third edge region along said first joining region, and said second edge region of the primary web layer has been synchronized to said fourth edge region of said cooperating web layer by a second, substantially permanent affixing of said second edge region to said fourth edge region layer along said second joining region.

13. The process as recited in claim 1, wherein said first edge region of the primary web layer has been synchronized to said third edge region of said cooperating web layer by a first, temporary attaching of said first edge region to said third edge region along said first joining region, and said second edge region of the primary web layer has been synchronized to said fourth edge region of said cooperating web layer by a second, temporary attaching of said second edge region to said fourth edge region layer along said second joining region.

14. The process as recited in claim 1, further comprising:

a lateral spacing of said first portion of the cooperating web layer away from said first portion of the primary web layer by a discrete cross-directional distance; and a placing of a first supplemental layer at an interposed location between said first portion of the cooperating web layer and said first portion of the primary web layer, said first supplemental web layer having a pair of laterally opposed side edge regions.

15. The process as recited in claim 14, further comprising:

an attaching of said first portion of the cooperating web layer to one side edge region of said first supplemental web layer; and an attaching of said first portion of the primary web layer to another side edge region of said first supplemental web layer.

16. The process as recited in claim 14, further comprising:

a lateral spacing of said second portion of the cooperating web layer away from said second portion of the primary web layer by a discrete cross-directional distance; and a placing of a second supplemental layer at an interposed location between said second portion of the cooperating web layer and said second portion of the primary web layer, said second supplemental web layer having a pair of laterally opposed side edge regions.

17. The process as recited in claim 16, further comprising:

an attaching of said second portion of the cooperating web layer to one side edge region of said second supplemental web layer; and an attaching of said second portion of the primary web layer to another side edge region of said second supplemental web layer.

18. An apparatus for creating a shaped article, comprising:

a positioning mechanism which places of a cooperating web layer in a superposed facing relation with a primary web layer, said primary web layer having first and second, lateral side edge regions, and said cooperating web layer having third and fourth, lateral side edge regions;

a coordinating mechanism which synchronizes said first edge region of the primary web layer to said third edge region of said cooperating web layer along a first joining region, and synchronizes said second edge region of the primary web layer to said fourth edge region of said cooperating web layer along a second joining region to form a synchronized laminated web;

a partitioning mechanism which separates said laminated web along a serpentine division line to provide a first composite web and at least a second composite web, said first composite web having a first portion of said primary web layer combined with a first portion of said cooperating web layer, and said second composite web having a second portion of said primary web layer combined with a second portion of said cooperating web layer; and a relocating mechanism which pivots said first portion of the cooperating web layer substantially about said first joining region to lie laterally adjacent to said first portion of the primary web layer.

19. The apparatus as recited in claim 18, further comprising another relocating mechanism which pivots said second portion of the cooperating web layer substantially about said second joining region to lie laterally adjacent to said second portion of the primary web layer.

20. The apparatus as recited in claim 18, wherein said partitioning mechanism separates said laminated web along said serpentine division line in a configuration which extends longitudinally along an appointed medial section of the laminated web and undulates laterally with a periodically repeating pattern, said repeating pattern has including at least two different pattern-segments.

* * * * *